United States Patent
De Silvestri

(10) Patent No.: US 10,610,592 B2
(45) Date of Patent: Apr. 7, 2020

(54) TREATMENT OF MULTIPLE SCLEROSIS

(71) Applicant: Fabrizio De Silvestri, Terni (IT)

(72) Inventor: Fabrizio De Silvestri, Terni (IT)

(*) Notice: Subject to any disclaimer, the term of this patent is extended or adjusted under 35 U.S.C. 154(b) by 65 days.

(21) Appl. No.: 14/793,970

(22) Filed: Jul. 8, 2015

(65) Prior Publication Data
US 2016/0030566 A1 Feb. 4, 2016

(30) Foreign Application Priority Data
Aug. 6, 2014 (IT) ...................................... 14/00207

(51) Int. Cl.
| | |
|---|---|
| A61K 45/06 | (2006.01) |
| A61K 31/65 | (2006.01) |
| A61K 31/40 | (2006.01) |
| A61K 31/4196 | (2006.01) |
| A61P 25/14 | (2006.01) |
| A61P 25/28 | (2006.01) |
| A61P 25/00 | (2006.01) |
| A61K 9/48 | (2006.01) |

(52) U.S. Cl.
CPC .............. *A61K 45/06* (2013.01); *A61K 31/40* (2013.01); *A61K 31/4196* (2013.01); *A61K 31/65* (2013.01); *A61P 25/00* (2018.01); *A61P 25/14* (2018.01); *A61P 25/28* (2018.01); *A61K 9/4816* (2013.01)

(58) Field of Classification Search
CPC .... A61K 31/40; A61K 31/4196; A61K 31/65; A61K 45/06; A61P 25/00; A61P 25/14; A61P 25/28
USPC ........................................................ 514/154
See application file for complete search history.

(56) References Cited

U.S. PATENT DOCUMENTS

| | | | | |
|---|---|---|---|---|
| 8,623,362 B2 * | 1/2014 | Chen | ..................... | C07K 16/248 424/139.1 |
| 8,691,777 B2 * | 4/2014 | Arbiser | ................. | A61K 31/453 514/235.8 |
| 2004/0013643 A1 * | 1/2004 | Mach | ................... | A61K 31/225 424/85.6 |
| 2005/0049208 A1 * | 3/2005 | Kaufmann | ......... | A61K 31/4178 514/28 |
| 2007/0110685 A1 | 5/2007 | Auspitz et al. | | |
| 2007/0135504 A1 | 6/2007 | Marshall | | |
| 2013/0116215 A1 * | 5/2013 | Coma | ................... | A61K 31/165 514/108 |
| 2016/0354391 A1 * | 12/2016 | de Silvestri | ............ | A61K 31/40 |

FOREIGN PATENT DOCUMENTS

| | | | |
|---|---|---|---|
| WO | WO 2013/040206 | 3/2003 | |
| WO | WO 2005/117902 | 12/2005 | |
| WO | WO 2008/021970 | 2/2008 | |
| WO | WO 2015037023 A1 * | 3/2015 | ............. A61K 31/40 |

OTHER PUBLICATIONS

Luccarini et al., "Combined treatment with atorvastatin and minocycline suppresses severity of EAE", 2008, Experimental Neurology, 211(1), pp. 214-226.*
Shi et al., "The combination of minocycline and fluconazole causes synergistic growth inhibitionagainstCandida albicans: aninvitro interaction of antifungal and antibacterial agents", 2010, FEMS Yeast Res., 2010, pp. 885-893.*
Cornelia Lass-Florl, "Triazole Antifungal Agents in Invasive Fungal Infections A Comparative Review", 2011, Drugs, 71(18), pp. 2405-2419.*
Savarin, C., Bergmann, C.C., Viral-induced suppression of self-reactive T cells: Lessons from neurotropic coronavirus-induced demyelination, J. Neuroimmunol. (2017), http://dx.doi.org/10.1016/j.jneuroim.2017.01.003, (online print: 5 pages total).*
Fluconazole 50mg Capsules—Summary of Product Characteristics, Jan. 2014, Kent Pharmaceuticals Ltd. (Year: 2014).*
Payette and Grant-Kels, "Generic drugs in dermatology Part II", Mar. 2012, J. Acad. Dermatol. vol. 66, pp. 353.e1-353.e15.
Yang, et al., "Advances in treatment of multiple sclerosis" Apr. 2011, Journal, Zhongguo ji ceng yi yao, vol. 18; issue 21, pp. 3005-3007.
McCarey et al., Trial of Atorvastatin in Rheumatoid Arthritis (TARA): double-blind, randomized placebo-controlled trial, Jun. 2004, The Lancet, vol. 363, pp. 2015-2021.
De Clercq, Guanosine analogues as anti-herpesvirus agents, Nucleosides Nucleotides Nucleic Acids, Oct.-Dec. 2000; 19(19-12):1531-41.
Jeong Yeon Kim et al., "Atorvastatin inhibits osteoclastogenesis by decreasing the expression of RANDL in the synoviocytes of rheumatoid arthritis", Arthritis Research and Therapy, Biomed Central, London, GB, vol. 14, No. 4, Aug. 17, 2012 (Aug. 17, 2012), p. R187.
Haga, H. et. al., "Severe deficiency of 25-hydroxyvitamin D3 (25-OH-D3) is associated with high disease activity of rheumatoid arthritis," Clin Rheumatol, vol. 32, Jan. 15, 2013 (Jan. 15, 2013), pp. 629-633.

(Continued)

*Primary Examiner* — My-Chau T. Tran
(74) *Attorney, Agent, or Firm* — Mintz, Levin, Cohn, Ferris, Glovsky and Popeo, P.C.

(57) ABSTRACT

A composition for treating neurodegeneration, including an antibiotic, an antifungal agent, and a lipophilic potentiating agent in synergistically effective amounts. A method of treating neurodegeneration, by administering a synergistically effective amount of the composition to an individual suffering from neurodegeneration, and treating neurodegeneration. A method of reducing and/or eliminating symptoms of neurodegeneration, by administering a synergistically effective amount of the composition to an individual suffering from neurodegeneration, and reducing and/or eliminating the individual's symptoms of neurodegeneration. A method of reducing and/or eliminating lesions from neurodegeneration. A method of recovering mobility of an individual suffering from neurodegeneration.

15 Claims, No Drawings

(56) References Cited

OTHER PUBLICATIONS

Ogrendik, "Antibiotics for the treatment of rheumatoid arthritis," International Journal of General Medicine, vol. 7, Dec. 27, 2013, pp. 43-47.
Leventis and Patel, "Clinical aspects of vitamin D in the management of rheumatoid arthritis", Rheumatology, vol. 47 (2008):1617-1621.
Kostoglou-Athanassiou et al., "Vitamin D and rheumatoid arthritis" Therapeutic Advances in Endocrinology and Metabolism, vol. 3, issue 6 (2012):181-187.
Non-final Office Action with notification dated Apr. 6, 2017 from U.S. Appl. No. 14/429,097.
Office Action dated Mar. 22, 2018 from U.S. Appl. No. 14/417,818.
Office Action dated Aug. 24, 2017 from U.S. Appl. No. 14/417,818.
Office Action dated Apr. 25, 2016 from U.S. Appl. No. 14/417,818.
Office Action dated Dec. 31, 2018 from U.S. Appl. No. 14/417,818.
Office Action dated Jan. 31, 2017 from U.S. Appl. No. 14/417,818.
Office Action dated Jan. 12, 2016 from U.S. Appl. No. 14/794,856.
Office Action dated Jun. 13, 2016 from U.S. Appl. No. 14/794,856.
Office Action dated Oct. 3, 2017 from U.S. Appl. No. 15/376,953.
Office Action dated Jun. 20, 2018 from U.S. Appl. No. 15/376,953.

* cited by examiner

TREATMENT OF MULTIPLE SCLEROSIS

BACKGROUND OF THE INVENTION

1. Technical Field

The present invention relates to compositions and methods of treating neurodegeneration. More specifically, the present invention relates to compositions and methods of treating multiple sclerosis.

2. Background Art

Multiple sclerosis (MS) is a chronic disease in which the immune system of the individual attacks the central nervous system (CNS) and affects the nerve cells. When the immune system attacks the CNS, myelin and nerve fibers are damaged, making it difficult to communicate between the brain and the spinal cord. Nerve cells transmit electrical signals, called action potentials, through long fibers called axons, which are covered with an insulated, fatty substance, the myelin sheath. In an individual suffering from MS, the immune system attacks and damages the myelin sheath. This damage causes distorted or interrupted nerve signals traveling to and from the brain and spinal cord because the axons are no longer able to transmit signals effectively. The name "multiple sclerosis" is derived from multiple sclerosis scars (i.e. plaques or lesions) that are formed in the white matter of the spinal cord and brain.

There is no known specific cause of MS, and genetic, environmental, and viral infections can play a role in development of the disease. It is generally held that MS involves an immune-mediated process because an exact antigen has not yet been found. Correlations have been found in MS patients with environmental factors (such as being located in an area farther away from the equator causing lower levels of vitamin D production, toxins, diet) in a genetically susceptible individual. Viruses or other infectious agents can possibly also play a role in MS, such as Epstein-Barr virus responsible for mononucleosis, further discussed below. Combinations of these factors can also contribute to the disease. MS generally occurs for the first time between 15 and 50 years with a peak incidence in young adults, affecting twice as many women than men.

The disease can manifest with a wide range of neurological symptoms and can progress to total physical and cognitive disability, and is clinically assessed with EDSS (Expanded Disability Status Scale). There are many different symptoms of MS, including fatigue, numbness, walking and balance problems, bladder dysfunction, bowel dysfunction, vision problems, dizziness and vertigo, sexual dysfunction, pain, cognitive dysfunction, emotional changes, depression, and spasticity. MS can also take various forms, including relapsing-remitting (having clearly defined attacks of worsening neurological function) and progressive (having steadily worsening symptoms over time). The life expectancy for an individual with MS is approximately 5 to 10 years lower than that of a healthy person. Prognosis is difficult to predict and depends on many different factors. Generally, individuals experience a reduction in the regenerative capacity of their body with each new acute episode.

While there is no known cure for MS, there are several treatments available that are approved to reduce disease activity and disease progression for individuals who have relapsing MS. Some immunosuppressive or immunomodulatory treatments are given in quiescence periods between one episode and another. These include interferon beta-1a, interferon beta-1 b, glatiramer acetate, mitoxantrone, natalizumab, fingolimod, and teriflunomide. Non-steroidal anti-inflammatory drugs (NSAIDs) can also be given with each new acute episode (i.e. corticosteroids administered in the form of bolus injections, intramuscularly or orally). Several of these treatments are described below.

Interferon beta-1a (AVONEX®, Biogen, Idec) is made from a naturally occurring interferon. In controlled clinical trials in relapsing MS, those taking the medication had a reduced risk of disability progression, experienced fewer exacerbations, and showed a reduction in number and size of active lesions in the brain (as shown on MRI) when compared with the group taking a placebo. In a subsequent study of patients who had experienced a single demyelinating event in the optic nerve, spinal cord, or brainstem, and had lesions typical of MS on brain MRI, AVONEX® significantly delayed the time to a second exacerbation, and thus to a clinically definite diagnosis of MS. AVONEX® is administered by once-a-week intramuscular injection. Common side effects include flu-like symptoms. Related to interferon beta-1a is interferon beta-1 b (BETAFERON®, Bayer Health Care). Both of these drugs have anti-inflammatory properties and improve the integrity of the blood-brain-barrier.

Glatiramer acetate (COPAXONE®, Teva Pharmaceuticals) is an immunomodulator that is a random polymer of four amino acids found in myelin basic protein (glutamic acid, lysine, alanine, and tyrosine). Glatiramer acetate is thought to work as a decoy for the immune system. Glatiramer acetate has comparable efficacy to interferons. Administration is by subcutaneous injection. Side effects include flu-like symptoms and lumps at injection sites, and is not recommended during pregnancy. While quality of life can be improved, glatiramer acetate does not have an effect on the incidence of relapses.

Natalizumab (TYSABRI®, Biogen Idec) is another medication approved for MS treatment, as well as Crohn's disease. Natalizumab is a humanized monoclonal antibody against the cell adhesion molecule α4-integrin. Natalizumab is administered by intravenous infusion every 28 days. It is designed to impede movement of potentially damaging immune cells from the bloodstream across the blood-brain-barrier into the brain and spinal cord. Side effects include a risk of progressive multifocal leukoencephalopathy (PML) with fatal outcomes that can greatly outweigh the benefits of taking natalizumab.

Teriflunomide (AUBAGIO®, Genzyme) is an oral medication for relapsing-remitting MS. It is widely used in rheumatology in the form of its precursor levoflunamide. The main advantage of teriflunomide is that is a once-a-day oral capsule instead of an injection. However, there is potential hepatotoxicity with the need for monthly checks of liver transaminases and a very prolonged elimination time, up to 2 years. This treatment should not be used during pregnancy, and methods exist to accelerate the elimination of the drug in case of desired pregnancy.

Dimethyl fumarate (BG-12, TECFIDERA®, Biogen Idec) can be used in treatment of relapsing-remitting multiple sclerosis (RRMS), the most common form of MS. Dimethyl fumarate activates the Nrf2 pathway, reduces the activity and impact of inflammatory cells on the central nervous system (CNS), and can induce direct cytoprotective responses in CNS cells. These effects can enhance the CNS cells' ability to mitigate the toxic inflammatory and oxidative stress that play a role in MS pathophysiology. Phase III studies showed dimethyl fumarate reduced relapse rate and increased time to progression of disability. Administration is oral. Side effects include skin reactions (flushing/redness) and gastrointestinal disorders.

Alemtuzumab (LEMTRADA®, Genzyme) is a monoclonal antibody that binds to proteins (CD-52) on mature lymphocytes, targeting them for destruction. Alemtuzumab was used for years for treating chronic leukemia, but was withdrawn from the market to be reintroduced for multiple sclerosis with an increased price. It has high efficiency, but also frequent and serious side effects. Approximately 40% of patients develop thyroid autoimmune diseases, and hematologic and renal complications. The treatment therefore requires a precise monitoring program with monthly checks of the blood and urine examination, which must be planned for four years after the last infusion. Treatment includes a series of 5 daily infusions at the beginning and three infusions after a year. This therapy is not one that can be terminated or modified easily and it is not clear how to proceed in case of insufficient response to therapy. Alemtuzumab can be used only in patients with very active disease as defined in clinical or radiological exams, and not for those who have a stable path or no signs of active inflammation in MRI. Alemtuzumab is not currently approved in the US.

Laquinimod is an oral immunomodulator currently under investigation. It has been shown to slow the progression of disability and reduce rate of relapse.

Fingolimod is an oral immunomodulator that is restricted to patients with relapsing-remitting MS with high disease activity despite treatment with β-interferon or in patients with severe forms of the disease rapidly evolving. There are possible side effects for the liver, cardiac system, and eyes requiring special precautions.

In special situations, other immunosuppressive drugs (azathioprine, methotrexate, cyclophosphamide) can be used to block cell replication globally, thus slowing down the reaction of the immune system. Being potentially toxic drugs, also used in cancer chemotherapy, they are reserved for cases of MS with rapid progression and disabling that do not respond adequately to an immunomodulatory drug. The selection, prescription, and monitoring of these therapies requires special expertise.

Other treatments have been focused more on the effects of the Epstein-Barr virus in MS patients, generally from mononucleosis. By was of background, infectious mononucleosis (also referred to as "kissing disease", for its transmissibility through saliva) is a highly contagious infectious viral illness, caused by the Epstein-Barr virus (EBV). The virus targets B cells and the course is acute, usually 4-6 weeks in duration. In developed countries the disease typically affects younger adults, with a prevalence in adolescents, while in developing countries the illness is more frequently observed in childhood, often in the first five years of life (Straus, et al 1993). Mononucleosis is so-named due to increased levels of mononuclear cells (lymphocytes and monocytes) and mononuclear cell properties.

Over 90% of the adult population has been infected by the virus and have developed antibodies against viral antigens. Again, peak infection rates are noted during early childhood in developing countries, while infection rates tend to be highest between 15 and 25 years of age in industrialized countries. The course may be asymptomatic or indistinguishable from that of a flu syndrome or pharyngitis with minor symptoms. Classic symptoms of mononucleosis tend to occur in affected younger patients, while affected adults typically experience a milder illness, characterized by fever, malaise and weakness, all characteristic symptoms of multiple sclerosis and rheumatoid arthritis. Several studies have demonstrated that in patients afflicted with autoimmune diseases such as systemic sclerosis, ulcerative colitis, systemic lupus erythematosus and to a lesser extent, those with rheumatoid arthritis, Sjögren's syndrome, ankylosing spondylitis and Crohn's disease, the presence of Epstein-Barr stimulates the formation of an autoantibody that may contribute to the maintenance of the inflammatory state (Draborg, et al 2013). Similar, but rare forms of autoimmune disease are caused by other infections such as Herpesvirus (CMV, HHV-6), other viral forms (adenovirus, HIV, HAV, Rubella), *Streptococcus pyogenes* and *Toxoplasma gondii*. It should be noted that several studies have provided evidence that mononucleosis is a risk factor for multiple sclerosis (Thacker, et al 2006).

In some individuals, likely predisposed by congenital or acquired factors that alter the immune response against the virus, the primary infection is unrestrained, and the Epstein-Barr virus continues to replicate causing chronic active infection (CAEBV) or very severe chronic active infection (SCAEBV). This syndrome has been variously described, because of its similarity to other ill-defined illnesses such as chronic fatigue syndrome and hemophagocytosis syndrome, both correlated with EBV (Eligio, et al 2010). In the majority of cases, acute illness lasts no more than four weeks without any complications; however, immunodeficiency mononucleosis can be very serious disease and lethal for immunocompromised patients. In any case, the symptoms can persist for months after healing.

Additionally, contrary to commonly held beliefs, patients with CAEBV are more frequently diagnosed with lymphoid malignancies originated by T cells, NK cells and B lymphocytes, as observed in post-transplant lymphoproliferative disease who are also found to be EBV positive. EBV in particular, and other infectious agents that can cause mononucleosis type responses (CMV, toxoplasmosis, hepatitis viruses, HIV), are among the recognized causes of chronic fatigue syndrome, which may also compromise the endocrine system (Glser et al 2012). The symptoms of infectious mononucleosis lasts about a month and is followed by a period of convalescence characterized by weakness, of varying duration and is not to be confused with chronic fatigue syndrome. The assumption is that intense weakness during the acute phase of mononucleosis places the patient at greater risk of developing this complication. Other rare complications include orchitis, myocarditis, pericarditis, genital ulcers, neutropenia and interstitial pneumonia. A similar pathogenesis of fulminant hepatitis is not considered, which is very rare and primarily observed in people with severe immune deficiencies.

Pathogenesis is as follows. After binding to its receptor, EBV penetrates the B lymphocyte. Its DNA exists within the cell in two forms: an episomial form in which the viral DNA remains detached from human genomic material, and an integrated form in which DNA is incorporated into the host genome, without a specific site of integration. After infection of B lymphocytes, two processes can occur: In the first response which is characteristic of most viral infections, a viral replicative cycle ensues, resulting in lysis of the infected cell. This process is followed by the release of new viral particles, which will continue to infect other cells. The second response, typical of EBV and of a few other viruses, suggests a state of latency during which the virus does not multiply within the cell. This latent period can last for a very long time and may explain why an individual exposed to EBV can accommodate a number of infected cells throughout most of their lifetime. Following infection by B cells, the viral genome governs the synthesis of certain proteins, called Epstein Barr Nuclear Antigens (EBNA). It was originally believed that EBNA consisted of only one protein. It is now known that EBNA consist of six different proteins, numbered from EBNA-1 to EBNA-6. These proteins interfere with the cell's DNA by changing the expression of several genes and permanently activating B cells that go through a process of indefinite proliferation (cellular immortalization). This phenomenon has been studied in vitro by reproducing human lymphocytes infected with the virus. The cells were found to proliferate indefinitely under the influence of the viral proteins EBNA, three membrane proteins (LMP1-2A-2B) and two types of non-polyadenylated RNA (EBER1 and EBER2). The cell line produced is called a lymphoblastoid cell line (LCL). Furthermore, two processes are likely to occur following the infection of b cells: The first process involves the beginning of a viral replicative cycle and the death of the infected cells by lysis. This is followed by the release of new viral particles that will go on to infect other cells. The second, typical of EBV and of a few other viruses, produces a state of latency during which time, the virus does not multiply within the cell. This latency can last for several years, and thus explains why an individual who has been exposed to the EBV can accommodate a number of infected cells indefinitely.

Based on the expression of viral proteins, and expression of cell surface markers, three programs of viral latency were identified:

Latency I is characterized by the expression of EBNA-1, Q by the promoter (Qp), the EBER 1.2 and LMP2A. In vivo, the EBV persists for life in memory B cells of a healthy carrier. In pathological conditions, the expression of these three genes characterizes the pathology of Burkitt's lymphoma and its corresponding cell lines.

Latency II is characterized by the expression of EBNA-1, Q by the promoter (Qp) and also of LMP1, LMP2A, EBV Ebers. There can also be an expression of LMP2B. Latency II has been observed in Hodgkin's disease, nasopharyngeal carcinoma, lymphoma nasal NK/T, and primary effusion lymphomas.

Latency III is characterized by transcription of all nine latent proteins. EBNA 1-2-3-4-5-6 are transcribed by the promoter Wp/Cp. Use of this promoter is the defining characteristic of latency III. Such cells are lymphoblastoid cell lines and some lines of Burkitt's lymphoma in prolonged culture. Latency III is also found in lymphomas associated with EBV infection in immunocompromised individuals.

It is therefore plausible to assume that a person whose immune system is compromised from immortalization by T and B lymphocytes present with the Epstein Barr Virus. The state of immortalization described above acts as a potential trigger for chronic, degenerative inflammation. Movement of b cells from the circulatory system to the lymph system, and consequently through the blood-brain barrier, would appear to trigger a chronic inflammatory process resulting in a demand for the production of reactive T lymphocytes; a likely consequence of the degeneration of B cells affected and changed as described above. The lymphatic system consists of a fluid that has been enriched with substances saturated by interstitial fluid due to the normal drainage of tissues. Infection or tissue damage may increase the production of fluid, rich in a number of substances (in particular antigens) that can trigger immune responses. Sites that are conducive to microbe entry such as the gastrointestinal tract are rich in dendritic cells and can capture antigens. These microbial antigens as well as several chemical inflammation mediators are then released into the bloodstream and make their way to the lymph nodes where the fluid is filtered and recirculated. This process is the activation of the adaptive immune response. It is thought that the ability to eradicate transcription errors at the endocellular level originates with the proliferation of T lymphocytes.

A team of researchers led by scientists at The Scripps Research Institute (TSRI), have discovered a family of proteins that connect the immune system to lipids in the human body. "This is the first time that shows someone how to blend the immune system and lipid metabolism",— explains Luc Teyton, lead author of the study (2009). In the study, published in "Science", Teyton and colleagues examined the T cells known as "natural killers" (NK) (2009). According to the authors, these cells play a key role in the immune system and are involved in autoimmune diseases such as diabetes and cancer, although the exact mechanism of is not yet understood. NK T cells represent a middle ground between innate and adaptive immunity: they are produced in the thymus and, once mature, stimulate an adaptive immune response. This is much like other T cell receptors, but without the normal antigenic variability. "Innate" receptors or NK cells have the ability to recognize certain lipids are on the outer surface of many bacteria such as *Mycobacterium tuberculosis*, the bacterium that causes TB. The NK T cells are activated when they bind to a surface protein called CD1 that produces an unidentified binder lipid. Once activated, these T cells secrete large amounts of proteins as interferon-gamma and interleukin-4, which in turn activate helper T cells to fight pathogens. The binding of CD1 with lipids is not limited to the immune response, but is used to maintain normal homeostasis of the body. Teyton, et al., realizing that an additional protein was necessary to transfer the lipid to the CD1 molecule, identified a family of genes that code for proteins, such as prosaposin, involved in several pediatric neurological diseases. Teyton, et al. found that eliminating the genes that encode for prosaposin disabled NK T cells from binding to CD1 molecules.

Although much is known about the molecular pathways involved in viral reactivation, what triggers reactivation in vivo is not precisely understood. The presumption is it that occurs when latently infected B cells respond to unrelated infections (because B cell receptor stimulation triggers reactivation in B-cell lines). A recent article has elucidated how an Epstein-Barr reactivation can have concomitant unrelated infections (Odumade et al 2011). Thus, basic protection against infection could, in principle, reduce the likelihood of relapse. The idea of utilizing antibiotics to produce a similar reaction is not a novel one. At the moment there are ongoing clinical trials aimed at evaluating the role of minocycline (an antibiotic) in treating multiple sclerosis.

Statins, widely prescribed as agents capable of lowering cholesterol levels, can be an alternative treatment in the future in multiple sclerosis, to be used individually or in related therapies, since they have demonstrated potent immunomodulatory effects (Neuhaus, et al., 2005). Several studies have revealed the ability of statins to prevent and to reverse the chronic and relapsing experimental autoimmune encephalomyelitis, an experimental animal model of multiple sclerosis (Luccarini, et al. 2008). Furthermore, in vitro studies with human immune cells have shown the immunomodulatory action of statins comparable to that of interferon beta 1-b (Neuhaus et al., 2005). In vitro studies have revealed the ability of statins to reduce the expression of cell adhesion molecules induced by activation on T cells (Koh, Nippon Rinsho 2003), specifically inhibit the expression of integrin LFA-1 on T cells, ligand of ICAM-1, cell adhesion molecule expressed on the luminal surface of brain endothelial cells, thereby preventing the entry of inflammatory cells, like T cells, within the brain parenchyma. A reduction of matrix metalloproteinase-9 (MMP-9) a proteolytic enzyme that helps to promote "openness" of the blood-brain barrier and, therefore, boost transendothelial migration of inflammatory cells was observed in vitro. Statins at least in vitro, reduce the expression of chemokine receptors on T cells that is B (Koh C S, Nippon Rinsho 2003). The implication is that statins can be effective immunomodulatory agents that deserve consideration as a treatment of multiple sclerosis (C S Koh, Nippon Rinsho 2003). The science is promising, as a clinical study conducted on patients diagnosed with multiple sclerosis, and treated with simvastatin, revealed a significant decrease in the number of new lesions, as demonstrated by MRI gadolinium (Neuhaus O et al., 2005).

Acycloguanosine was considered for its ability as an anti-retroviral, its low toxicity, as well as its proven ability as an antifungal and a known preventive agent against Epstein Barr Virus, as indicated in 1993 by Lonnqvist, et al. Also, Vitamin D3, which is synthesized by keratinocytes via the stimulation induced by UV rays, acts as a hormone, and is able to perform an effective immune-stimulating effect, especially in subjects with chronic deficits.

There appears to be a positive interaction between minocycline and atorvastatin, as suggested by research on experimental autoimmune encephalomyelitis (EAE) induced in mice, wherein Luccarini et al (2008), demonstrated that combined treatment with atorvastatin and minocycline suppresses severity of EAE. Although this research has shown that this combination has the ability to reduce the severity of injuries subsisting in subjects suffering from a form of induced MS, it has never been tested on human subjects. While minocycline and atorvastatin provides a positive interaction, patients would still be at risk of the side effect of fungal infections due to the use of antibiotics.

Each of the above treatments have a number of serious side effects and induce a constant weakening of the body, without providing any form of real recovery or rebalancing of the body. Therefore, there remains a need for a treatment for multiple sclerosis that can reduce symptoms at all stages of the disease as well as reduce and eliminate existing lesions while eliminating side effects.

SUMMARY OF THE INVENTION

The present invention provides for a composition for treating neurodegeneration, including an antibiotic, an antifungal agent, and a lipophilic potentiating agent in synergistically effective amounts.

The present invention provides for a method of treating neurodegeneration, by administering a synergistically effective amount of a composition including an antibiotic, an antifungal agent, and a lipophilic potentiating agent to an individual suffering from neurodegeneration, and treating the neurodegeneration.

The present invention also provides for a method of reducing and/or eliminating symptoms of neurodegeneration, by administering a synergistically effective amount of a composition including an antibiotic, an antifungal agent, and a lipophilic potentiating agent to an individual suffering from neurodegeneration, and reducing and/or eliminating the individual's symptoms of neurodegeneration.

The present invention also provides for a method of reducing and/or eliminating lesions from neurodegeneration, by administering a synergistically effective amount of a composition including an antibiotic, an antifungal agent, and a lipophilic potentiating agent to an individual suffering from neurodegeneration, and reducing and/or eliminating lesions in the central nervous system and/or peripheral nervous system.

The present invention further provides for a method of recovering mobility of an individual suffering from neurodegeneration, by administering a synergistically effective amount of a composition including an antibiotic, an antifungal agent, and a lipophilic potentiating agent to the individual, and recovering mobility and motor control in the individual's limbs and extremities.

DETAILED DESCRIPTION OF THE INVENTION

The present invention generally provides for compositions and methods of treating neurodegeneration, and especially multiple sclerosis.

"Neurodegeneration" as used herein, refers to any condition that results in loss of structure and/or function of neurons, especially in the CNS and/or peripheral nervous system. The composition of the present invention can be used to treat neurodegenerative diseases characterized by a demyelinating form and/or intoxication, or the presence of viruses such as Epstein Barr virus or other members of the same family of herpesviruses, and especially multiple sclerosis. Other demyelinating neurodegenerative disease can include, but are not limited to, myelinoclastic disorders (Devic's disease, inflammatory demyelinating diseases), leukodystrophic disorders (CNS neuropathies, central pontine myelinolysis, myelopathies (Tabes dorsalis), leukoencephalopathies (progressive multifocal leukoencephalopathy), and leukodystrophies), Guillain-Barre syndrome, chronic inflammatory demyelinating polyneuropathy, anti-MAG peripheral neuropathy, Charcot-Marie-Tooth disease, copper deficiency associated conditions, and progressive inflammatory neuropathy. Preferably, the neurodegeneration causes lesions and demyelination of nerves.

"Multiple sclerosis" as used herein, can refer to autoimmune-type relapsing-remitting, progressive, or degenerative forms of multiple sclerosis.

"Recovering mobility" as used herein refers to recovering at least some, and preferably most or all, use of limbs and extremities such that an individual can move without as much restriction and/or pain as previously as well as with more control. Preferably, recovering mobility includes recovering the ability to walk and balance without aids such as a walker, cane, or assistance of an individual.

The composition of the present invention includes an antibiotic, an antifungal agent, and a lipophilic potentiating agent in synergistically effective amounts. More preferably, the composition includes a tetracycline antibiotic, a triazole antifungal agent, and a lipophilic statin in synergistically effective amounts. Even more preferably, the composition includes minocycline, fluconazole, and atorvastatain. Preferably, the composition is a pharmaceutical composition including pharmaceutically acceptable excipients.

The antibiotic can be any suitable antibiotic and is preferably a tetracycline antibiotic. Most preferably, the tetracycline antibiotic is minocycline ((2E,4S,4aR,5aS,12aR)-2-(amino-hydroxy-methylidene)-4,7-bis(dimethylamino)-10, 11,12a-trihydroxy-4a,5,5a,6-tetrahydro-4H-tetracene-1,3, 12-trione). Minocycline is long-acting and has a longer half-life than other tetracyclines. Minocycline is lipid soluble and easily penetrates the brain and CNS. Any other equivalent forms can be used. Other tetracycline antibiotics with the same function that can be used include, but are not limited to, tetracycline, chlortetracycline, oxytetracycline, demeclocycline, methacycline, tigecycline, or doxycycline. In general, tetracycline antibiotics act to inhibit protein synthesis and the binding of aminoacyl-tRNA to the mRNAribosome complex. The dose of the tetracycline antibiotic can be from 25 mg to 500 mg, every 12 hours, depending on age and weight. Preferably, the dose is from 50 mg to 100 mg. Most preferably, the dose is 100 mg. It should be understood that a lower dose can be used because of the synergy of the components.

The antifungal agent can be any suitable antifungal agent, and preferably, a triazole antifungal agent or acycloguanosine (2-Amino-1,9-dihydro-9-((2-hydroxyethoxy)methyl)-6H-purin-6-one), also known as aciclovir. The triazole antifungal agent is preferably fluconazole. Fluconazole is an antifungal agent with a triazole ring structure (2-(2,4-Difluorophenyl)-1,3-bis(1H-1,2,4-triazol-1-yl)propan-2-ol). The presence of the substituent triazole increases the selectivity of the drug for fungal cytochrome P450 (lower toxicity for humans), water solubility, and resistance to degradation compared to imidazole derivatives. Fluconazole acts by interfering with synthesis of the fungal cell membrane by inhibiting cytochrome P450 enzyme 14α-demethylase. It causes inhibition of the enzyme lanosterol 14-demethylase C thus blocking the synthesis of ergosterol, one of the main constituents of the fungal cell membrane. Failure of the formation of ergosterol causes an increase in membrane permeability followed by cell death. It is active both in vitro and in vivo against *Candida* spp. (*C. albicans, C. glabrata, C. tropicalis, C lusitaniae, kirusci C., C. parapsilosis, C. guilliermandi*); about 90% of the isolated strains of *Candida* were susceptible to concentrations of fluconazole of from 0.25 to 6.4 mg/L. Typically, fluconazole acts as a fungistatic (replication inhibitor) toward typical *Candida*. Fluconazole is an effective drug in the treatment of localized and systemic fungal infections typically incurred by *Candida*, the overgrowth of which is a known effect of broad-spectrum antibiotics, as well as other fungal pathogens. Any other equivalent forms can be used. Other triazole antifungal agents with the same function that can be used include, but are not limited to, albaconazole, efinaconazole, isavuconazole, itraconazole, voriconazole, pramiconazole, ravuconazole, terconazole, or posaconazole. The dose of the triazole antifungal agent can be 25 mg to 400 mg every 12 hours, depending on age and weight. Preferably, the dose is between 50 mg and 100 mg. Most preferably, the dose of the triazole antifungal agent is 50 mg. It should be understood that a lower dose can be used because of the synergy of the components.

The lipophilic potentiating agent can be any suitable agent that is able to cross the blood-brain barrier. Preferably, the lipophilic potentiating agent is a lipophilic statin. The lipophilic statin is preferably atorvastatin (LIPITOR®, Pfizer) ((3R,5R)-7-[2-(4-Fluorophenyl)-3-phenyl-4-(phenylcarbamoyl)-5-propan-2-ylpyrrol-1-yl]-3,5-dihydroxyheptanoic acid). Atorvastatin is a competitive inhibitor of HMG-CoA reductase, reducing cholesterol. Lipophilic statins are effective at crossing the blood-brain barrier into the CNS. Any other equivalent forms can be used. Other lipophilic statins with the same function that can be used include, but are not limited to, lovastatin, simvastatin, cerivastatin, fluvastatin, and mevastatin. The dose of the lipophilic statin can be 5 mg to 40 mg every 12 hours, depending on age and weight. Most preferably, the dose is 20 mg, or even 10 mg in order to avoid rhabdomyolysis. It should be understood that a lower dose can be used because of the synergy of the components.

Preferably, the composition is in a single oral dosage form, such as a pill, capsule, or tablet, with each of the antibiotic, antifungal agent, and lipophilic potentiating agent contained therein or within a coating. Different combinations or each component can be included within the oral dosage form or within its coating. The composition can be tailored to provide different release profiles as needed or desired for a particular patient, such as, but not limited to, sustained release, prolonged release, or immediate release. The antibiotic, antifungal agent, and lipophilic potentiating agent can each have the same release profiles or different release profiles. However, other dosage forms and routes can be used as detailed below. Preferably, the dosage form is gastroresistant.

Acycloguanosine can also be administered in combination with the recommended daily allowance of Vitamin D for its immunomodulatory properties believed to reverse the immune-deficiencies found in patients with autoimmune diseases.

The preferred combination of components in the composition is 100 mg minocycline, 20 mg atorvastatin, and 50 mg fluconazole in a single dosage form.

Preferably, the composition is administered once every 12 hours, considering the half-lives of the components. Other times of administration can be used depending on the dosage. While beneficial effects can be experienced upon taking the first dose, it is preferred that an individual continue treatment for days, weeks, months, and/or years. Treatment can be 45 days or longer, Length and frequency of treatment is contingent upon the form of disease, i.e., primary progressive or relapsing-remitting.

The three components of the composition (antibiotic, antifungal agent, and lipophilic potentiating agent) produce a potentiated effect as opposed to their effect alone because they act synergistically together. This can result in a lower dose of each component required to be effective and reduced side effects. In the examples below, no noteworthy side effects were experienced. The combination of an antibiotic and the lipophilic potentiating agent implement the elimination and eradication of capsids immortalized by a consequent inflammatory process and induce a regenerative process of injured areas. In order to reduce the potential, albeit reduced, toxicity from the prolonged ingestion of tetracycline antibiotics, it is necessary to add an antifungal agent for its fungistatic properties. The combination of minocycline, atorvastatin, and fluconazole was chosen because of the low toxicity of the same, high ability to pass the blood-brain barrier, the same half-life of the drugs, and the ability to interact synergistically with each other. The ability to penetrate into the tissues of atorvastatin lipid allows, if it is administered in conjunction with a suitable excipient, to boost the ability of the immune modulating minocycline and to increase the neuroprotective ability of the statin. The antifungal agent was added to reduce the presence of fungi, or the proliferation of the same in an environment overloaded from antibiotic such as minocycline, or already infested by appearances such as *Candida albicans*. Often the presence of fungi is high due to previous infections brought by the imbalance caused by the massive use of corticosteroids, immunosuppressants, and the like, which already by themselves would be eligible to trigger a mechanism of excessive proliferation of the same that, once past the blood brain barrier through the presence of the same into the blood stream, are able to trigger a mechanism of systemic intoxication and amplify the inflammatory process. In particular, fluconazole is the preferred antifungal agent due its the half-life being equal to that of atorvastatin and minocycline and it acts primarily in the lipophilic environment. Fluconazole was able to enhance the synergistic effect of the atorvastatin and minocycline combination, therefore producing a synergistic effect with all three components of the composition of the present invention.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The present invention provides for a method of treating neurodegeneration, by administering a synergistically effective amount of a composition including an antibiotic, antifungal agent, and lipophilic potentiating agent to an individual suffering from neurodegeneration. The neurodegeneration can be caused by any disease described above, and especially multiple sclerosis. Preferably, the antibiotic is a tetracycline antibiotic, the antifungal agent is a triazole antifungal agent, and the lipophilic potentiating agent is a lipophilic statin. Most preferably, the tetracycline antibiotic is minocycline, the triazole antifungal agent is fluconazole, and lipophilic statin is atorvastatin. The antibiotic, antifungal agent, and lipophilic potentiating agent can also be any of those described above. Preferably, the composition is administered in a single dosage form orally once every 12 hours. Preferably, the single dosage form includes 100 mg minocycline, 20 mg atorvastatin, and 50 mg fluconazole. Treatment can last 45 days or longer.

Treating neurodegeneration, especially multiple sclerosis, can include reducing and/or eliminating symptoms experienced with neurodegeneration as well as reversing the cause of neurodegeneration. As further demonstrated in the examples below, the composition of the present invention can reduce and/or eliminate symptoms of neurodegeneration and multiple sclerosis such as by improving and recovering mobility and motor control in limbs and extremities, decreasing fatigue and increasing energy levels, improving and restoring balance, improving and restoring the ability to walk and be upright, improving and restoring urinary and bowel control, reducing muscle pain, and reducing and eliminating paresthesia. Any combination of these improvements can be experienced by the individual depending on their symptoms when beginning treatment. The composition of the present invention can also reduce lesions (in size and amount) in the central nervous system and/or peripheral nervous system that cause neurodegeneration, especially multiple sclerosis. The method can reduce an individual's EDSS value by at least two points.

The present invention therefore also provides for a method of reducing and/or eliminating symptoms of neurodegeneration, by administering a synergistically effective amount of a composition including an antibiotic, antifungal agent, and lipophilic potentiating agent to an individual suffering from neurodegeneration, and reducing and/or eliminating the individual's symptoms of neurodegeneration. The neurodegeneration can be caused by any disease described above, and especially multiple sclerosis. The composition can be any of those described above. Preferably, the composition is administered in a single dosage form orally. Preferably, the single dosage form includes 100 mg minocycline, 20 mg atorvastatin, and 50 mg fluconazole. The symptoms reduced and/or eliminated are described above.

The present invention also provides for a method of reducing and/or eliminating lesions from neurodegeneration, by administering a synergistically effective amount of a composition including an antibiotic, antifungal agent, and lipophilic potentiating agent to an individual suffering from neurodegeneration, and reducing and/or eliminating lesions in the central nervous system and/or peripheral nervous system. The neurodegeneration can be caused by any disease described above, and especially multiple sclerosis. The composition can be any of those described above. Preferably, the composition is administered in a single dosage form orally as described above. Preferably, the single dosage form includes 100 mg minocycline, 20 mg atorvastatin, and 50 mg fluconazole. Preferably, the lesions are reduced at least 40%, and more preferably, at least 50%. Reducing the lesions results in a recovery of function of the body and a reduction/elimination of the symptoms of multiple sclerosis. In other words, the composition is able to remyelinate damaged nerves (i.e. demyelinated nerves) in the CNS that have been damaged due to neurodegeneration.

The present invention provides for a method of recovering mobility of an individual suffering from neurodegeneration, by administering a synergistically effective amount of a composition including an antibiotic, antifungal agent, and lipophilic potentiating agent to the individual, and recovering mobility and motor control in the individual's limbs and extremities. The neurodegeneration can be caused by any disease described above, and especially multiple sclerosis. The composition can be any of those described above. Preferably, the composition is administered in a single dosage form orally as described above. Preferably, the single dosage form includes 100 mg minocycline, 20 mg atorvastatin, and 50 mg fluconazole. Preferably, mobility and motor control is increased enough such that the individual can walk and balance without aid.

In preliminary mice studies, MS was induced in mice as experimental autoimmune encephalomyelitis (EAE) and administration of atorvastatin and minocycline let to improvements clinically and immunologically. There was a significant anti-inflammatory and neuroprotective activity. Severity and histological consequences were reduced and progression of the disease was slowed. This was confirmed by a visible reduction of the areas of brain lesion by 40%.

While atorvastatin and minocycline were synergistic, additional synergism was experienced when fluconazole was added in experiments detailed below in MS human subjects. These MS subjects showed significant functional recovery as early as the first week of administration, through 45 days (extending over the time of suspending the therapy) confirmed by the administration of test and evaluation boards (Scale Bartel Index, analysis of muscle imbalance, Kendall, and two minute walking test (2MWT)). An increase in efficacy was experienced when the combination of three compounds was used. The use of fluconazole reduced the side effect nearly to zero of an increase in abdominal volume likely caused by the use of prolonged minocycline, which as an antibiotic may have produced an increase in the proliferation of *Candida albicans*. None of the patients experienced negative reactions with any medication already used, and none had any relapse during the treatment.

To date, all subjects involved have a significant improvement in quality of life and recovered much autonomy. In one subject, it has been observed through magnetic resonance that there was a remission of demyelinated areas of approximately 40%.

The composition of the present invention is advantageous in that each component individually has been proven effective, and in combination produces a synergistic effect not shown before in MS patients. Each component has low toxicity and a long period of permanence in the market. The composition is effective in reducing the incidence of MS on quality of life of the patient. Further, no relapses have been experienced by subjects in the examples below.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Protocol

In each of the examples below, the composition administered included 100 mg minocycline, 20 mg atorvastatin, and 50 mg fluconazole in a single oral dosage form (capsule).

Example 1

P.R. is an Italian woman, 45 years of age. Height 170 cm, weight 55 kg. The patient is married, has no children, and lives with her husband. She is college educated and works as a teacher. She initially went to see a neurologist with complaints of fatigue and widespread paresthesias in the legs. She was initially placed on a regimen of Rebif 44 Chelation therapy.

The patient reports having angioplasty of the jugular veins. There is no trauma reported in her medical history. She is a smoker, but does not consume alcohol. The diagnosis of relapsing-remitting MS was made in June 2006, when MRI evidenced corticospinal lesions. The patient has limb motor deficits, balance disorder, tremors and incontinence. The patient is not self-sufficient, needs aids to eat, and uses a wheelchair.

Pre-treatment EDSS score: 8.

The patient has only taken Rebif 44 from the time of diagnosis. P.R. discontinued Rebif 44 prior to starting treatment with this drug regimen. P.R. started drug treatment (the composition of the present invention) on Aug. 1, 2014. She was administered one capsule every 12 hours. The patient reported recovery of mobility in the limbs by the 6th day of therapy. By day 12, the patient reported a significant decrease in fatigue on the 12th. P.R. reported that by the 15th day of therapy, she had enough energy to start the exercise regime for the upper extremities on a regular basis. After 45 days of treatment, it was noted that her balance and control of her upper and lower extremities had improved. It was evident that the patient could ambulate for short distances without assistance, and could remain upright unassisted for at least two minutes. P.R also indicated a partial recovery of the urinary and bowel control, as well as the ability to feed herself, unassisted.

Post-treatment EDSS score: 7.

Example 2

Z.A. is a 57 year old Italian woman. Height 175 cm, weight 64 kg. The patient is married, and has no children. She is a college graduate, but is not currently employed.

Z.A. sought treatment with a neurologist for profound fatigue, weakness of the lower extremities and difficulty maintaining balance. She was treated with methotrexate and cortisone on a weekly basis.

Her medical history is unremarkable. Z.A. does not smoke or consume alcohol. The diagnosis of relapsing-remitting MS was made in January 2006, when an MRI evidenced demyelinating lesions. The patient presents with hypotonia and motor deficits in the lower limbs, balance disorder, and urinary incontinence. She was not self-sufficient and used a wheelchair Pre-treatment EDSS score: 7.5.

Z.A. began drug treatment (the composition of the present invention) on Jan. 12, 2015. She was administered one capsule every 12 hours. All other therapy was discontinued just prior to the initiation of therapy. By the $8^{th}$ day of therapy, the patient reported an initial recovery of mobility in the lower extremities. Z.A. reported a significant decrease in fatigue on the 12th day of therapy. It is reported that by the 20th day of therapy, the patient had enough energy to start the exercise regime at least for the upper extremities, on a regular basis. After 45 days of treatment, the patient exhibited improvement in balance and motor control of the limbs. Z.A. could walk for short distances without a wheelchair or an aide. She reported improved bladder and bowel function.

Post-treatment EDSS score: 6.

Example 3

S.C. is a 55 year old Italian woman. Height 172 cm, weight 67 kg. The patient is married and lives with her husband. S.C. graduated from college and worked as a sociologist. At her initial neurological visit she reported "tingling" to both feet and difficulty moving her right leg. Her past medical history includes mononucleosis at age 25, pollen allergies, and childhood diseases (measles, chicken pox and mumps). Medications: cortisone, Rebif 22, Copaxone, Avonex, aminopyridine.

The patient denies any prior surgery. The patient's medical record notes an accident that resulted in parasthesias to the lower extremities. She does not smoke and consumes alcohol occasionally. The diagnosis of relapsing-remitting MS was made in July 2012, following a hospitalization due to an investigation of a paresthesias. They were found by examining RM principles of injury to the corticospinal level. The patient has right lower limb motor deficits, trouble maintaining balance, and chronic fatigue. The patient uses a cane for assistance ambulating.

Pre-treatment EDSS score: 6.

S.C. began treatment with cortisone with initiation of Rebif 22 after 7 months for sensitization to the drug. She also began a new therapy of Copaxone injections which was immediately suspended for suspected allergic reaction shortly after initiation of therapy. S.C. continued treatment with AVONEX aminopyridine and then suspended treatment after six months. S.C. started drug treatment (the composition of the present invention) Mar. 9, 2015. She was administered one capsule every 12 hours. Upon initiation of therapy the patient was not taking any other medication. She reported a significant decrease in fatigue on the 2nd day of treatment, and the absence of muscle pain in the limbs by Day 4. The patient also reported recovery of mobility of the right lower limb. It is reported that by the 3rd day of treatment, she had enough energy to start the exercise regime on a regular basis with a focus on the upper limbs. She reports that her family believes that she appears to be in better health. At the end of 45 days of treatment, the patient experience a marked improvement in balance and motor control of the limbs. The use of the cane has been markedly reduced.

Post-treatment EDSS score: 5.

Example 4

C.R. is a 40 year old Italian man. Height 172 cm, weight 70 kg. The patient is separated from his wife and son, and lives alone. The patient worked in law enforcement. C.R. went to see a neurologist with complaints of widespread fatigue, paresthesias to the extremities, and difficulty maintaining balance. Drugs taken: Rebif 44, Copaxone.

No significant medical history. Non-smoker, does not consume alcohol. The diagnosis of relapsing-remitting MS was made in June 2007, MRI evidenced lesions in the brain and spine. The patient presents with numbness in the legs especially the right side, balance disorder, and urinary urgency.

Pre-treatment EDSS score: 3.5.

Treatment with Copaxone was suspended shortly after initiation of therapy due to an allergic reaction. He then started therapy Rebif 44 for five years. C.R. initiated therapy (with the composition of the present invention) on Oct. 22, 2013. He was administered one capsule every 12 hours. The patient was taking no other medication at the initiation of treatment. A significant decrease in fatigue was reported on the 2nd day of therapy. C.R. reported that by the 4th day of therapy, he had enough energy to start the exercise regime on a regular and ongoing basis. The patient also reported an improvement of mobility in the limbs from the 5th day. After 45 days of treatment, the patient experience a marked improvement in balance and motor control of the lower extremities, and can now walk without any signs of weakness or imbalance. It should be noted a marked reduction in paresthesias occurred. Recent MRI results have demonstrated a reduction of the lesions greater than 50%.

Post-treatment EDSS score: 1

Example 5

P.C. is a 49 year old Italian woman. Height 170 cm, weight 60 kg. The patient lives with her husband, and has no children. She does not work. At her first visit with her neurologist she presented with complaints of widespread fatigue, diplopia, and weakness in her right leg. Medications: Corticosteroids, Copaxone, Interferon, Chelation therapy.

The patient has an unremarkable medical history. She does not smoke, nor does she consume alcohol. The diagnosis of relapsing-remitting MS was made in June 2008, by the presence of lesions evident on MRI. The diagnosis was confirmed by CSF analysis. P.C. presents with hypotonia and motor deficits in the legs and balance disorder. She is not self-sufficient and uses a walker.

Pre-treatment EDSS score: 7.5.

The patient has been on a course of corticosteroids associated along with Copaxone. This regimen was discontinued after 6 months, at which time the patient was administered chelation therapy for one year. Following discontinuation of chelation therapy, the patient no longer used any other drugs. P.C. started drug treatment (the composition of the present invention) Dec. 6, 2014. She was administered one capsule every 12 hours. The patient reported initial recovery of mobility in the limbs from the 3rd day of treatment. P.C. reported a decrease in fatigue on the 10th day of therapy. It is reported that by the 15th day of therapy, that she had enough energy to start the exercise regime at least for the upper extremities on a regular basis. After 45 days of treatment, P.C. reported an improvement in balance and motor control of all 4 extremities.

Post-treatment EDSS score: 6.

Example 6

F.J. is a 49 year old African-American woman. She is 172 cm, 63 kg. The patient is married and resides with her husband and 4 of her 5 adult children. F.J. is doctorate prepared, and was working as a hospital administrator in November 2012, when she began to experience what she described as "parasthesias" in both feet and right leg. She presented at her first neurology appointment with symptoms that included "pins and needles" feelings to both feet and her right leg, several episodes of vertigo over 7 years, and extreme fatigue for several years. Her past medical history includes mumps at age 3, 2 vaginal births and 1 C-section in 1982, 1990, and 1995, respectively, mononucleosis at age 30, major depressive disorder at age 38, and a course of shingles at age 41, affecting her right rib cage. Medications include Lexapro 20 mg daily, Wellbutrin XL 150 mg daily, Neurontin 400 mg 3 times daily, Baclofen 10 mg 3 times daily, Provigil 100 mg daily as needed for fatigue, Gilenya 0.5 mg daily, Xanax 0.25 every 6 hours as needed for anxiety. Surgical history includes repair of left ruptured fallopian tube secondary to ovarian cyst torsion, Harrington rod replacement for progressive scoliosis at age 22, cholecystectomy at age 31, cardiac ablation for supraventricular tachycardia at age 35, supracervical hysterectomy at age 46. She has a history of tobacco use and consumes alcohol socially. Diagnosis of relapsing-remitting multiple sclerosis was made in March 2013 after finding of increased IgG levels in CSF, significant conduction delays in EMG studies, small lesions noted on CT scan along with presenting symptoms. By history, the treating physician estimated that the patient has probably had MS for approximately 10 years. The patient is fully functional, presents with no motor deficits, and exercises several days a week. She has described several episodes over the past 5 years where she felt physically unable to rise from her bed and needed assistance due to low energy levels.

EDSS score prior to initial drug therapy: 5.

The patient reports a period in 2006, when she experienced vertigo and tinnitus over a 4 month period. She underwent extensive testing with an ears, nose and throat specialist who reported "no findings". F.J. was started on a course of injectable Copaxone 20 mg daily, in March 2012. The patient continued to complain of fatigue while on therapy and decreased episodes of parasthesias to the extremities. F.J. also reported an intense and constant throbbing pain that traveled from the base of her skull to the sacrum. All spinal MRI's to date have been negative for lesions or malignancies. Although the patient reported no adverse systemic effects, she found the injection site swelling and pain intolerable after 9 months, and stopped therapy. F.J. requested a change to oral therapy, and was worked up to begin 0.5 mg or oral Gilenya in March 2014. The patient has reported no side effects from Gilenya. She has been treated twice with high dose steroid infusion therapy for relapses in June 2014 when she reported acute problems with balance, and in October 2014, when she began to experience spasms in bilateral hands and feet. Baclofen 10 mg 3 times daily was added to her regime at this time. The patient also reported a persistent feeling of "brain fog", for which no medications were prescribed.

F.J. began treatment with the composition of the present invention on Mar. 26, 2015, implementing a course of one capsule every 12 hours. The patient reports that she ceased taking all medications with the exception of Wellbutrin and Lexapro (and Xanax as needed) upon initiation of treatment. She reported a significant decrease in back pain by day 3 of therapy, and an absence of back pain by day 5. The patient also reported the complete absence of fatigue by day 7, and reports that she has been informed by family members that her speech is much more organized than it had been for the past 3 years. F.J. had stopped exercising due to increased and chronic fatigue. She reports that by day 10 of therapy, she has had enough energy to begin her rigorous exercise regime. By day 21 of therapy, the patient reported that all of her symptoms attributed to multiple sclerosis were no longer present.

Post-treatment EDSS score: 2.3.

Example 7

A.B. is an Italian woman 37 years old. Height 165 cm, weight 79 kg. The patient is married and lives with her husband and two adult children. A.B. graduated and worked as a clerk. On a first visit, neurological symptoms presented as "tingling" with both feet, numbness in the right leg and slight difficulty moving the right forearm, and excessive fatigue. Her past medical history includes 2 vaginal deliveries, mononucleosis at the age of 19, minor depressive disorder, an episode of diplopia in 34 years. Drugs taken include two azathioprine 50 mg tablets a day associated with steroids.

No surgery and no trauma are recorded in her medical history. Smokes and consumes alcohol occasionally. The diagnosis of relapsing-remitting MS was made in June 2009, following a hospitalization due to an investigation of paresthesias in the lower right corner. They were found by examining RM small lesions on the corticospinal level. The patient has the right lower limb motor deficits, and reported two cases of recurrence over the past five years.

Pre-treatment EDSS score: 5.

Although the patient has not taken any medication for three years, she began after a therapy azathioprine associated with steroid administration. Therapy was discontinued after a year and a half due to sensitization to the drug (gastrointestinal toxicity). A.B. started treatment with the composition of the present invention Oct. 13, 2014, one capsule every 12 hours, and at the time of initiation of therapy not taking any medication. She reported a significant decrease in fatigue on the $2^{nd}$ day of treatment, and the absence of muscle pain in the limbs from the $6^{th}$ day. The patient also reported a principle of recovery of the right lower limb mobility, and reports that the family said that she appears to show a state of better health. It is reported that by the $3^{rd}$ day of treatment, she had enough energy to start the exercise regime on a regular basis. At the end of the 45 days of treatment, the patient experienced a marked improvement in balance and motor control of the limbs.

Post-treatment EDSS score: 3.5.

Example 8

So-Called is an Italian woman 55 years old. Height 172 cm, weight 67 kg. The patient is married and lives with her husband. So-Called graduated and worked as a sociologist. At the first visit neurological symptoms presented as "tingling" to both feet and difficulty moving her right leg. Her past medical history includes mononucleosis at age 25, pollen allergies, and childhood diseases (measles, chicken pox, and mumps). Medications include cortisone, Rebif 22, Copaxone, and Avonex aminopyridine.

The patient had no surgery, but an accident with paresthesia in the legs is recorded in her medical history. She does not smoke, but consumes alcohol occasionally. The diagnosis of relapsing-remitting MS was made in July 2012, following a hospitalization due to an investigation of a paresthesias in the lower right corner. They were found by examining RM principles of injury to the corticospinal level. The patient has right lower limb deficits, trouble maintaining balance and chronic fatigue, and requires walking aids such as a cane.

Pre-treatment EDSS score: 6.

So-Called has started treatment with cortisone associated with Rebif 22, and suspended treatment after 7 months for sensitization to the drug. She began a new therapy with Copaxone that was immediately suspended for suspected allergic reaction. She continued with Avonex aminopyridine and then suspended after six months.

She started treatment with the composition of the present invention Mar. 9, 2015, one capsule every 12 hours, at the time of initiation of therapy she was not taking any medication. She reported a significant decrease in fatigue on the $2^{nd}$ day of treatment, and the absence of muscle pain in the limbs from the $4^{th}$ day. The patient also reported a principle of recovery of the right lower limb mobility, and reports that members of her family said that they could see that she appears to show a state of better health. It is reported that by the $3^{rd}$ day of treatment, she had enough energy to start the exercise regime on a regular basis with a focus on the upper limbs. At the end of the 45 days of treatment, the patient experienced a marked improvement in balance and motor control of the limbs. The use of the cane is reduced to the minimum necessary.

Post-treatment EDSS score: 5.

Example 9

Z.U. is an Italian man 50 years old. Height 170 cm, weight 78 kg. The patient is married and lives with his wife. Z.U. graduated and worked as an architect. At first visit, neurological symptoms presented such as loss of balance, numbness in his right arm and mild difficulty walking. His past medical history includes stomach ulcers and gastrointestinal disorders. Drugs taken: none. He is a non-smoker and does not consume alcohol.

The diagnosis of relapsing-remitting MS was made in May 2010, based on the investigations due to a steady loss of balance and difficulty walking without aid. RM small lesions were examined in the spinal cord. The patient has mild motor deficits in the limbs, minor difficulties in coordinating arms, and difficulty maintaining balance.

Pre-treatment EDSS score: 4.

The patient has never used drugs as problems related to the digestive system limited the administration of therapies proposed (type 2 Azathioprine 50 mg tablets once a day associated with steroids).

Z.U. started treatment with the composition of the present invention on Oct. 21, 2014, one capsule every 12 hours, at the time of initiation of therapy he was not taking any medication. He reported a significant decrease in fatigue on the $1^{st}$ day of treatment and the absence of muscle pain in the limbs from the $2^{nd}$ day. The patient also reported a recovery of limb control, and reports that the family said that it looks like he appears to show a state of better health. He also reported that from day 1 of therapy, he has had enough energy to start the exercise regime on a regular basis. At the end of the 45 days of treatment, the patient experienced a marked improvement in balance and motor control of the limbs.

Post-treatment EDSS score: 2

Example 10

C.R. is an Italian man 40 years old. Height 172 cm, weight 70 kg. The patient is separated, has a son, lives alone, graduated and worked in law enforcement. At first visit, neurological symptoms presented of widespread fatigue, paresthesia emisoma dx and difficulty maintaining balance. Drugs taken include 44 Rebif and Copaxone. There was no trauma recorded in his medical history. He is a non-smoker and does not consume alcohol.

The diagnosis of relapsing-remitting MS was made in June 2007 with an examination of RM lesions in the brain and spine. The patient presents with numbness in the legs, especially the right side, balance disorder, and urinary urgency.

Pre-treatment EDSS score: 3.5.

The patient from the onset of the disease has taken Copaxone and suspended for adverse reaction. He then started therapy with Rebif 44 for 5 years. He started treatment with the composition of the present invention on Oct. 22, 2013, one capsule every 12 hours, at the time of initiation of therapy he was not taking any medication. He reported a significant decrease in fatigue on the $2^{nd}$ day of therapy. The patient also reported an improvement of mobility in the limbs from the $5^{th}$ day. It is reported that by the $4^{th}$ day of therapy, he had enough energy to start the exercise regime on a regular and ongoing basis. At the end of the 45 days of treatment, the patient experienced a marked improvement in balance and motor control of the limbs so that he can walk without problems. It should be noted there was a marked reduction in paresthesia emisoma right. Recent investigations RM show a reduction of the lesions greater than 50%.

Post-treatment EDSS score: 1.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A composition for treating multiple sclerosis, said composition comprising: 100 mg minocycline, 50 mg fluconazole, and 20 mg atorvastatin in a single dosage form.

2. A method of treating multiple sclerosis comprising:
   administering a composition comprising minocycline in an amount of 25 mg to 500 mg, fluconazole in an amount of 50 mg to 100 mg, and atorvastatin in an amount of 5 mg to 40 mg once every 12 hours to an individual suffering from multiple sclerosis, wherein the composition is in a single oral dosage form; and treating the multiple sclerosis.

3. The method of claim 2, wherein said administering step is further defined as administering the composition for at least 45 days.

4. The method of claim 2, wherein the minocycline is present in the amount of 50 mg to 500 mg.

5. A method of treating multiple sclerosis comprising steps of:

administering a composition comprising 100 mg minocycline, 50 mg fluconazole, and 20 mg atorvastatin in a single dosage form to individual suffering from multiple sclerosis; and treating the multiple sclerosis.

6. The method of claim 5, wherein said treating step comprises reducing and/or eliminating symptoms of multiple sclerosis selected from the group consisting of improving and recovering mobility and motor control in limbs and extremities, decreasing fatigue and increasing energy levels, improving and restoring balance, improving and restoring the ability to walk and be upright, improving and restoring urinary and bowel control, reducing muscle pain, reducing and eliminating paresthesia, and combinations thereof.

7. The method of claim 5, wherein said treating step comprises reducing lesions in size and amount in the central nervous system.

8. The method of claim 5, wherein said treating step further comprises reducing the individual's Expanded Disability Status Scale (EDSS) value by at least two points.

9. The method of claim 5, wherein the multiple sclerosis chosen from the group consisting of relapsing-remitting, progressive, and degenerative.

10. A method of reducing and/or eliminating symptoms of multiple sclerosis, comprising:

administering a composition comprising 100 mg minocycline, 50 mg fluconazole, and 20 mg atorvastatin in a single dosage form to an individual suffering from multiple sclerosis; and reducing and/or eliminating the individual's symptoms of multiple sclerosis.

11. The method of claim 10, wherein said reducing and/or eliminating step comprises improving and recovering mobility and motor control in limbs and extremities, decreasing fatigue and increasing energy levels, improving and restoring balance, improving and restoring the ability to walk and be upright, improving and restoring urinary and bowel control, reducing muscle pain, reducing and eliminating paresthesia, and combinations thereof.

12. A method of reducing and/or eliminating lesions in the central and/or peripheral nervous system of an individual suffering from multiple sclerosis comprising:

administering a composition comprising 100 mg minocycline, 50 mg fluconazole, and 20 mg atorvastatin in a single dosage form to an individual suffering from multiple sclerosis; and reducing and/or eliminating lesions in the central nervous system and/or peripheral nervous system.

13. The method of claim 12, wherein said reducing and/or eliminating step is further defined as reducing lesions by at least 40%.

14. The method of claim 13, wherein said reducing and/or eliminating step is further defined as reducing lesions by at least 50%.

15. A method of recovering mobility of an individual suffering from multiple sclerosis comprising:

administering a composition comprising 100 mg minocycline, 50 mg fluconazole, and 20 mg atorvastatin in a single dosage form to the individual suffering from multiple sclerosis; and recovering mobility in the individual suffering from multiple sclerosis.

* * * * *